(12) United States Patent
Hanania et al.

(10) Patent No.: US 12,265,200 B2
(45) Date of Patent: Apr. 1, 2025

(54) NORMAL-TO-PLANE SURFACE PLASMON MODE FOR ANGLE-AND-POLARIZATION INDEPENDENT OPTOMECHANICAL SENSING

(71) Applicant: Samsung Electronics Co., Ltd., Suwon-si (KR)

(72) Inventors: Haeri Park Hanania, San Gabriel, CA (US); Hyuck Choo, Yongin-Si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 64 days.

(21) Appl. No.: 17/512,658

(22) Filed: Oct. 27, 2021

(65) Prior Publication Data
US 2023/0003920 A1 Jan. 5, 2023

Related U.S. Application Data

(60) Provisional application No. 63/217,655, filed on Jul. 1, 2021.

(51) Int. Cl.
| | | |
|---|---|---|
| G02B 1/00 | (2006.01) | |
| A61B 3/16 | (2006.01) | |
| G01L 11/02 | (2006.01) | |
| G02B 5/00 | (2006.01) | |

(52) U.S. Cl.
CPC .............. *G02B 1/002* (2013.01); *G01L 11/02* (2013.01); *G02B 5/008* (2013.01); *A61B 3/16* (2013.01); *A61B 2562/0285* (2013.01); *G02B 2207/101* (2013.01)

(58) Field of Classification Search
CPC ........ G02B 5/008; G02B 1/002; G02B 1/007; G02B 26/06; G02B 1/005; G02F 1/292; G02F 2202/30
See application file for complete search history.

(56) References Cited

U.S. PATENT DOCUMENTS

| | | | |
|---|---|---|---|
| 8,462,334 B2 | 6/2013 | Lu et al. | |
| 2013/0065777 A1 | 3/2013 | Altug et al. | |
| 2013/0170018 A1* | 7/2013 | Domash | G02B 26/007 |
| | | | 359/320 |
| 2015/0041937 A1* | 2/2015 | Yu | H01L 27/14625 |
| | | | 438/70 |
| 2016/0350445 A1* | 12/2016 | Dowski, Jr. | H04N 23/57 |
| 2018/0341090 A1* | 11/2018 | Devlin | G03F 7/40 |
| 2020/0141871 A1 | 5/2020 | Chang et al. | |
| 2020/0257194 A1* | 8/2020 | Sorin | B81C 1/0046 |

(Continued)

OTHER PUBLICATIONS

Li et al., "Flexible, low-loss, large-area, wide-angle, wavelength-selective plasmonic multilayer metasurface", J. Appl. Phys. 114, 133104 (Year: 2013).*

(Continued)

*Primary Examiner* — Jonathan Y Jung
(74) *Attorney, Agent, or Firm* — Renaissance IP Law Group LLP (57) ABSTRACT

The present example embodiment relates generally to creating a specific nanostructure on a substrate to improve the angle independence of a surface plasmon resonance mode. It may comprise a metamaterial structure comprising nanostructures located in a pattern on or within a substrate. The nanostructures may be paraboloid shaped and periodic.

16 Claims, 9 Drawing Sheets

(56) References Cited

U.S. PATENT DOCUMENTS

2021/0208312 A1* 7/2021 Zhang ................. C23C 16/405
2021/0405256 A1* 12/2021 Sachet .................. G02B 5/207
2022/0120969 A1* 4/2022 Karabchevsky ....... G02B 6/262
2022/0342119 A1* 10/2022 Leskosek ............... G02B 1/002

OTHER PUBLICATIONS

Choi, Kiwoon et al., "Nano-Tailoring the Surface Structure for the Monolithic High-Performance Antireflection Polymer Film," Advanced Materials, vol. 22, No. 33, 2010, pp. 3713-3718.

Ding, Fei et al., "Gradient Metasurfaces: Fundamentals and Applications," ARXIV.org, Cornell University Library, 2017, 83 pages.

European Extended Search Report for Application No. 22174540.9, mailed Nov. 25, 2022.

Ogawa, Shinpei et al., "Metal-Insulator-Metal-Based Plasmonic Metamaterial Absorbers at Visible and Infrared Wavelengths: A Review," Materials, vol. 11, No. 3, 2018, 18 pages.

Xu, Zefeng et al., "A Stretchable Terahertz Parabolic-Shaped Metamaterial," Advanced Optical Materials, vol. 7, No. 19, 2019, 10 pages.

* cited by examiner

NORMAL-TO-PLANE SURFACE PLASMON MODE FOR ANGLE-AND-POLARIZATION INDEPENDENT OPTOMECHANICAL SENSING

CROSS REFERENCE TO RELATED PATENT APPLICATIONS

This application claims priority to U.S. Provisional Patent Application Ser. No. 63/217,655, filed on Jul. 1, 2021, the disclosure of which is hereby incorporated by reference.

TECHNICAL FIELD

The present example embodiment relates generally to creating a specific nanostructure on a substrate to improve the angle independence of a surface plasmon resonance mode.

BACKGROUND

Measuring intraocular pressure can be challenging. Current techniques require expensive, cumbersome sensors. These sensors may require the eye to be still and for sensors to be placed at a fixed angle of incidence on the eye. Metamaterials, which may include plasmonic materials, on the other hand, hold potential for a variety of improvements to current methods, including decreased size and decreased angle dependence. Metamaterials currently are not angle-independent and cannot be embedded in the eye. There exists a need for a metamaterial that is angle-independence or has reduced angle dependence.

SUMMARY

The example embodiment provides a metamaterial structure, comprising a substrate, and nanostructures located in a pattern on or within the substrate, wherein the nanostructures are paraboloid shaped and periodic. A further example embodiment provides for a method to fabricate a metamaterial surface, comprising depositing a nanostructure metal on a substrate, and forming paraboloids from the nanostructure metal.

DETAILED DESCRIPTION

Metamaterials are capable of interacting with light in unconventional ways. A metamaterial may comprise of an array of nanostructures distributed across a surface. A spectrum, such as the visible spectrum, may interact with the nanostructures. A plasmonic material may be a type of metamaterial. There may be a surface plasmon (SP) mode, where the spectrum may cause a charge distribution on the metamaterial's nanostructured surface that may oscillate between a positive and negative charge periodically.

A surface plasmon mode may occur when the nanostructures have a certain shape and distribution. In some embodiments, the nanostructures may be shaped like paraboloids and the distribution may comprise overlapping tiles that may be hexagonal in shape. The surface plasmon mode, also known as normal-to-plane mode, together with the distribution of the nanostructures, may interact together to reflect one wavelength from the spectrum at a much greater intensity than other wavelengths, which may be known as a "peak wavelength reflected" or a "target wavelength." The nanostructures may be capable of operating in normal-to-plane mode. For many metamaterials, the angle of incidence may change the peak wavelength reflected. However, with a paraboloid-shaped nanostructures and the overlapping tile distribution, a change in angle of incidence may result in a markedly lower change of peak wavelength reflected compared to other shapes and distributions of nanostructures.

This greatly reduced dependence of the peak wavelength on the angle of incidence may lead to the term "angle independence" being used herein to describe this phenomenon.

Furthermore, when the nanostructure is stretched or compressed, the peak wavelength reflected may change. This property of changing the peak wavelength reflected may be used to measure pressure changes when the nanostructure is part of a pressure sensing device. Lastly, a change in peak wavelength may also occur if the nanostructure is exposed to a liquid on its surface. The liquid may interact with the nanostructures surface to change the peak wavelength shift. This property of changing peak wavelength shift may be used to identify chemicals in a chemical analysis sensor.

While previous processing techniques may allow for shapes including disks and pillars, none may allow for paraboloid or other rounded shapes that may be manufactured at the nanometer scale. As will be described, these processing techniques may enable a normal-to-plane mode nanostructure.

Figure 1:
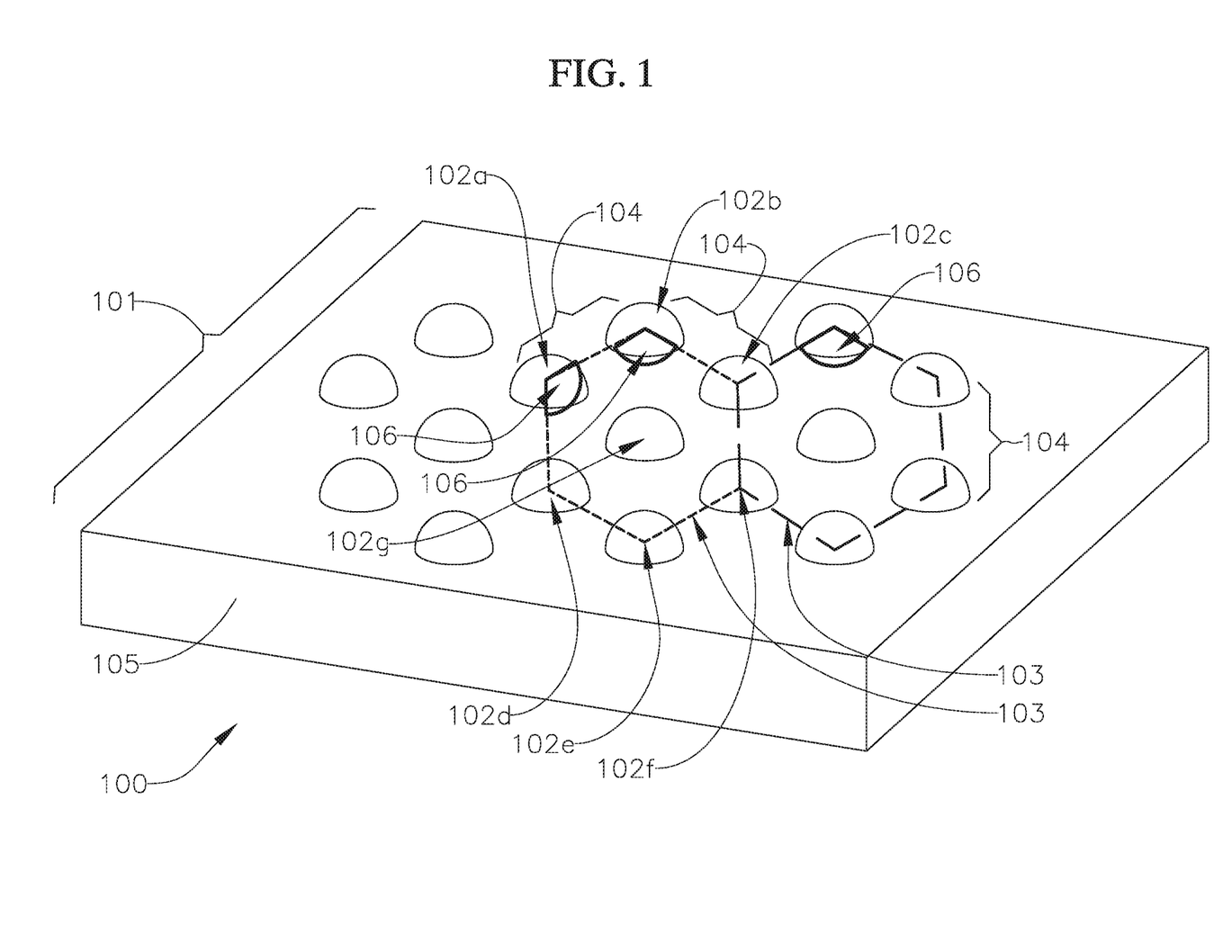
FIG. 1 depicts an example embodiment of a nanostructure of the present example embodiment.

FIG. 1 depicts an example embodiment of a structure 100. Structure 100 may comprise nanostructures 101. Nanostructures 101 may be embedded within a substrate 105, or may be on top of a substrate 105. Nanostructures 101 may be organized in a pattern 103.

In some embodiments, nanostructures 101 may be gold, aluminum, silver, copper, aluminum-doped zinc oxide, indium tin oxide, titanium nitride, indium gallium arsenide, tungsten oxide, titanium-tungsten or any other metals or metal alloys, however, they may be made of other materials as well, not listed. Nanostructures 101 may be distributed or located in a pattern 103 on or within substrate 105. Pattern 103 may be periodic, which may be a repeatable distribution of nanostructures. Pattern 103 may have equidistant nanostructures 101, such as a hexagonal pattern. Pattern 103 may have both equidistant and non-equidistant structures (i.e., are partially equidistant), such as a square pattern where some neighboring nanostructures may be equidistant while other neighboring nanostructures have a different distance (e.g., diagonal neighbors). Pattern 103 may be periodic or it may be semi-periodic, where there may be a repeatable pattern for some of the nanostructures while there is a non-repeatable pattern for other parts of the nanostructure.

In some embodiments, pattern 103 may form a tessellation, which may be a tile. The tessellation may be overlapping or may be non-overlapping. Pattern 103 may be a periodic pattern that may provide an equidistant spacing of nanostructures 101. Equidistant may be an approximation where the distances between nanostructures are approximately equal but may have variations due to the accuracy limitations of fabrication techniques, which will be described later in more detail.

In some embodiments, pattern 103 may be six-sided, which may be a hexagonal tile pattern, which may also be known as a hexagonal lattice. Nanostructures 101 may form a hexagonal tile pattern, where six nanostructures can form the six vertices of a hexagon. In some embodiments, nanostructures 102a-f may form pattern 103 for the example case of a hexagonal pattern. There may be an additional nanostructure embedded within pattern 103, such as at the center of pattern 103 which may be nanostructure 102g. Nanostructure 102g may form a vertex of another pattern 103 of nanostructures.

Nanostructure 102a may be a first distance 104 away from nanostructure 102b. First distance 104 may be known as a lattice constant, and may be the distance between the center of nanostructure 102a and the center of nanostructure 102b. Furthermore, nanostructure 102b may be a first distance 104 from nanostructure 102c. First distance 104 may be based on a target wavelength of structure 100 and may be the wavelength that structure 100 may be designed for peak wavelength reflection, which will be described in more detail in FIG. 2. In some embodiments, first distance 104 may be between 60 nm and 600 nm. In other embodiments, first distance 104 may be greater for longer target wavelengths and may be less for shorter target wavelengths.

The angle between the edge formed by nanostructure 102a to nanostructure 102b and nanostructure 102b to nanostructure 102c may be a first angle 106. In some embodiments, if pattern 103 is hexagonal, first angle 106 may be about 120 degrees. The first distance 104 and first angle 106 may be approximately the same for all edges and angles of pattern 103 for all subsequent nanostructures 102a-f.

In alternate embodiments, the shape of pattern 103 may be any shape that can be tessellated. In some embodiments, pattern 103 may maintain the equidistant and equal-angle properties for all nanostructures as described previously. In another embodiment, pattern 103 may not be have fully equidistance and equal-angled nanostructures. In another embodiment, pattern 103 may not be periodic, that is, there may be a fixed pattern where nanostructures 101 may not be equidistant from each other. As may be readily appreciated, pattern 103 may alternatively be expressed as a tiling of the triangles (e.g., equilateral triangles or isosceles triangles) that make up a hexagonal or square pattern.

In some embodiments, substrate 105 may be a flexible or stretchable material that may allow for flexing of the substrate, such as polydimethylsiloxane (PDMS), but may be other materials as well. In another embodiment, substrate 105 may be rigid, such as nickel, but may be other materials as well. In some embodiments, substrate 105 may be between 100 nm to 50 μm thick.

Figure 2A:
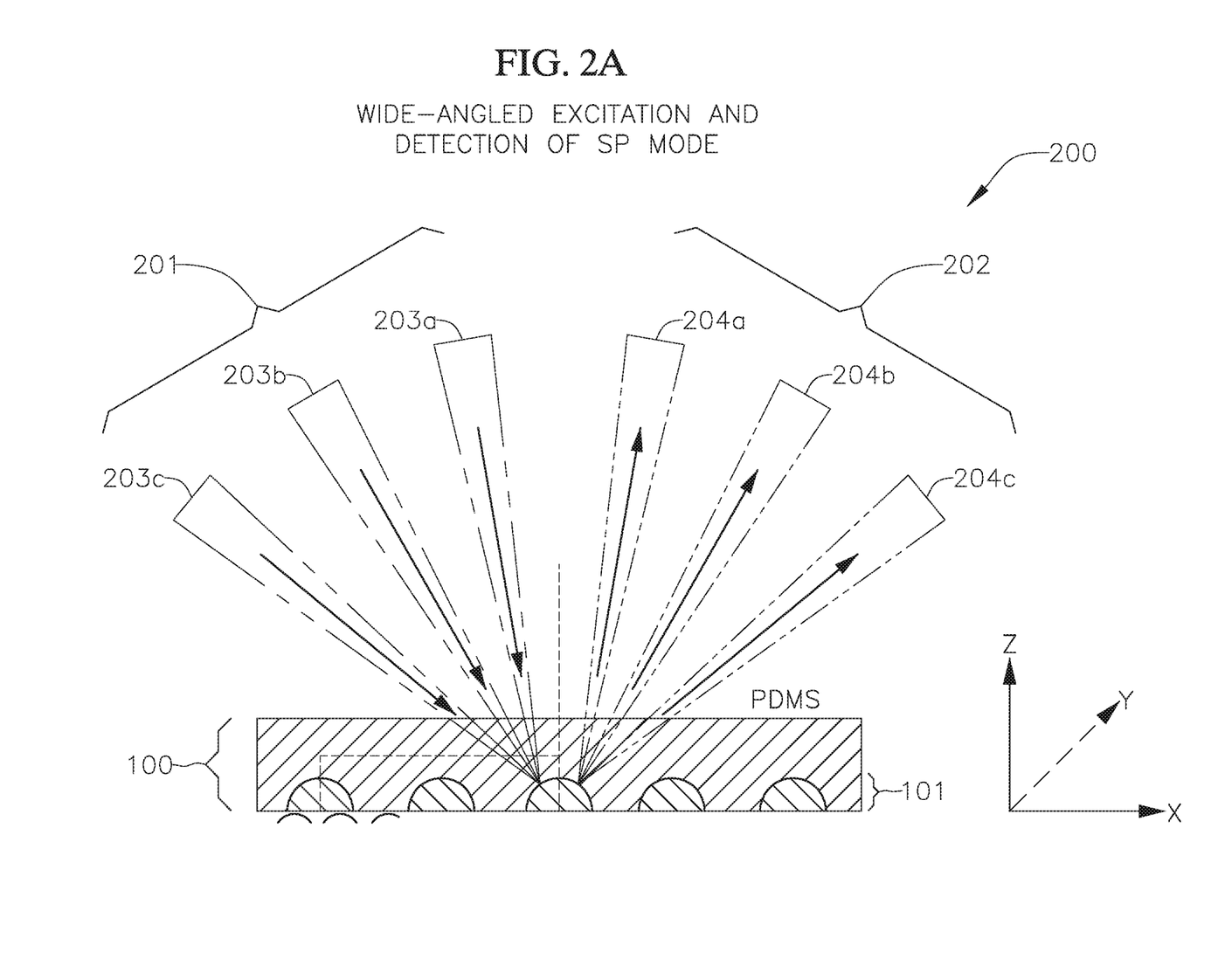
FIG. 2A depicts a side view of the nanostructure of FIG. 1.

FIG. 2A depicts a side view 200 of structure 100 of FIG. 1. A spectrum 201 may travel onto structure 100 at a first angle of incidence 203a, which may also be known as a first angle 203a. First angle 203a may be any angle between 0 degrees (parallel to the plane of structure 100) and 90 degrees (perpendicular to the plane of structure 100). In some embodiments, spectrum 201 may comprise any wavelength or range of wavelengths, which may be known as broadband light, in the visible and near-infrared spectrum. In another embodiment, spectrum 201 may be in a different spectrum range, such as near-infrared, ultraviolet, microwave, or other wavelength range. There may be a second angle of incidence 203b and a third angle incidence 203c, which may also be any angle between 0 degrees and 90 degrees.

Spectrum 201 may interact with structure 100 and produce a reflected spectrum 202, which may be reflected from structure 100 at a first angle of reflection 204a. First angle of reflection 204a may be any angle between 90 degrees (perpendicular to the plane of structure 100) and 180 degrees (parallel to the plane of structure 100). Reflected spectrum 202 may have a peak wavelength, which may also be known as the target wavelength, that is reflected and all other wavelengths may have little to no reflection, which will be described in more detail below. There may also be a second angle of reflection 204b and a third angle of reflection 204c, which may be any angle between 90 degrees and 180 degrees. The first angle of reflection 204a may depend on the first angle of incidence 203a. The second angle of reflection 204b may depend on the second angle of incidence 203b, and so on.

In some embodiments, reflected spectrum 202 may be approximately the same for all angles of angles of incidence 203a-c. That is, the response of structure 100 to spectrum 201 may be angle-independent. Angle-independence may not be truly independent, that is, there may be some variations in the exact peak wavelength reflected in reflected spectrum 202 based on the angles of incidence 203a-c, but such angle dependence is greatly reduced compared to other metamaterials.

The peak wavelength reflected may vary slightly based on the angle of incidence 203a-c. For example, spectrum 201 may be broadband light spanning 500 nm-1000 nm. First angle of incidence 203a may be 6030 degrees, second angle 203b may be 45 degrees, and third angle 203c may be 3060 degrees. In response, reflected spectrum 202 may have a first peak wavelength of about 600 nm for first angle 203a, a second peak wavelength of about 602 nm for second angle 203b, and a third peak wavelength of about 604 nm for a third angle 203c. The first, second, and third peak wavelengths may be substantially similar so as to apply the term "angle-independent," however, there may still be small wavelength variations in reflected spectrum 202 based on the angles of incidence 203a-c.

In another embodiment, the peak wavelength for any given angle may change when structure 100 is stretched or compressed. If structure 100 is stretched or compressed, reflected spectrum 202 may have a new peak wavelength that is different than the first peak wavelength. The difference between the new peak wavelength and the first peak wavelength may be used to infer a change in pressure, as described further below.

In another embodiment, the peak wavelength may change when structure 100 is exposed to and/or in contact with a liquid or other material. The composition of the liquid or other material may be determined based on the change in peak wavelength. If structure 100 exposes nanostructures 101 and a liquid or new material is in contact with nanostructures 101, such as a fluid, reflected spectrum 202 may have a different peak wavelength relative to the peak wavelength in absence of the material. The difference between the first and different peak wavelengths may be used to infer information such as the presence of a certain material in contact with structure 100, and may be discussed in more detail later in the description.

Structure 100 may also be polarization-independent. That is, the reflected spectrum 202 may be polarization independent. For example, spectrum 201 may have different transverse electric (TE) or transverse magnetic (TM) polarizations. That is, for any polarization of spectrum 201, reflected spectrum 202 may be approximately the same.

Figure 2B:
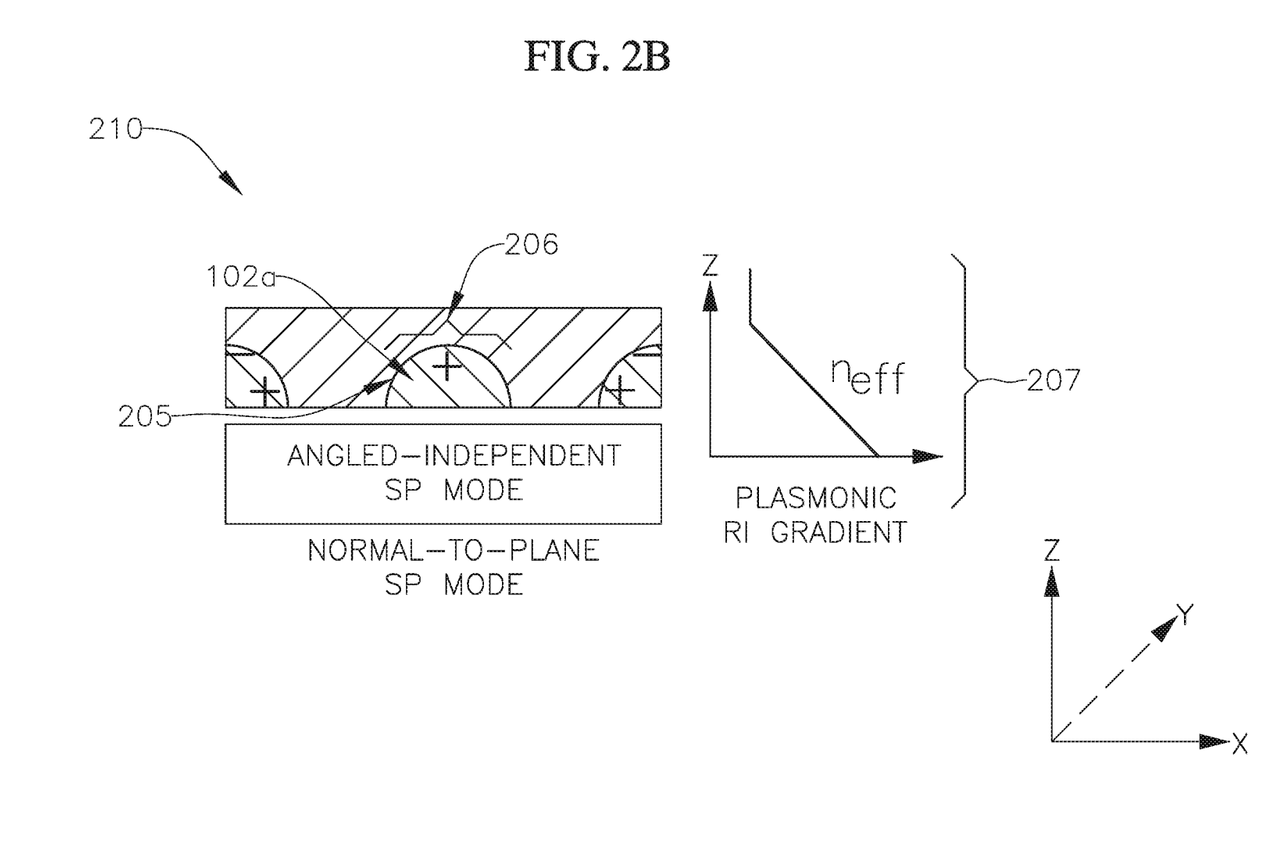
FIG. 2B depicts a side view of a nanostructure of the present example embodiment.

FIG. 2B depicts a side view 210 of nanostructure 102a. There may be a z-axis and an x-axis shown, with a y-axis going into the plane of side view 210. The z-axis may depict the height of nanostructure 102a and the x-axis may depict the width of nanostructure 102a. At the bottom of the z-axis, nanostructure 102a may be at its widest point, which may be its diameter. The diameter of the nanostructure 102a is defined as the intersection of the nanostructure 102a and the base substrate it is formed on. The cross section of nanostructure 102a may be shown along the Z-X plane. In some embodiments, the diameter of nanostructure 102a at its base may be 200 nm, but may be other diameters between 10 nm and 2000 nm. The height of nanostructure 102a may be 100 nm, but may be other heights, for example, between 36 nm and 168 nm.

The dimensions of nanostructure 102a may change based on the target wavelength and the material used. Resolving the height and the diameter of the nanostructures for a target wavelength requires solving for two variables (height and diameter), and as one varies within an acceptable range, the other will vary accordingly. In some embodiments, the height of nanostructure 102a may be between 12% and 56% of the first distance 104. In some embodiments, the diameter of nanostructure 102a may be between 40% to 80% of the first distance 104.

The height and diameter of nanostructure 102a may be determined by checking for normal-to-plane mode for a fixed lattice constant and varying the diameter d and height h of nanostructure 102a. There may be parameters f and r, which may be used in conjunction with experimental testing to confirm a normal-to-plane mode and to determine a range of acceptable height and diameter values. Aspects of some embodiments may implement the RI gradient principle into a periodic plasmonic array and realize a 'normal-to-plane' SP mode that is angle-and-polarization independent, and experimentally demonstrate for the first time plasmonics-based angle-and-polarization independent strain and pressure sensing in the near IR region. The filling factor f (e.g., f=d/a) and aspect ratio r (e.g., r=h/d) of the plasmonic RI gradient array play a role in enabling the normal-to-plane mode. In addition, $|\Delta\lambda|$ and the operation range of $\theta$ of the normal-to-plane mode can be optimized by varying f and r. The experiment may compare variables f to r, defined as:

$f$=diameter of nanostructure 102a/the lattice constant (i.e. first distance 104) and $r$=height of nanostructure 102a/diameter of nanostructure 102a.

Figure 2C:
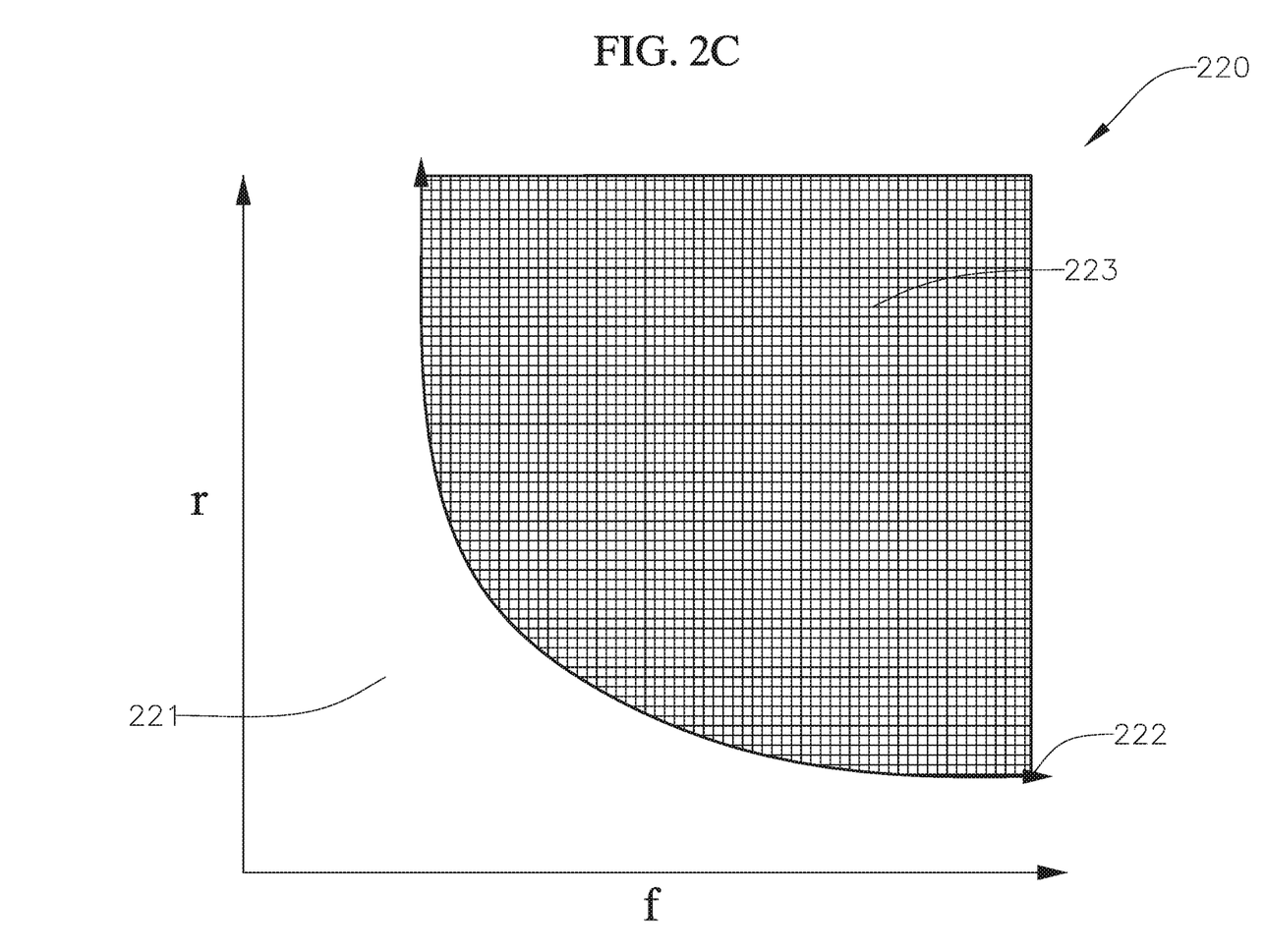
FIG. 2C depicts an experimental test based on experimentally varied height and diameter values of the nanostructures of FIG. 1.

Referring to FIG. 2C, there may be an experimental test 220 based on experimentally varied height and diameter values, and which may compare the variables f and r for a fixed lattice constant value. A lattice constant value may be determined based on a target wavelength, and the final height and diameter of nanostructure 102a may be determined based on the results of test 220. Test 220 may reveal regions 221 and 223 and there may be a border line 222. Region 223, which may include border line 222, may be a region in which a normal-to-plane mode exists and may allow for the angle independent behavior. Region 221 may be a region in which normal-to-plane mode does not exist.

For height and diameter values of nanostructure 102a in region 221, the angle of incidence of spectrum 201 may result in a large change in peak wavelength shift of reflected spectrum 202, which will be described in more detail later in FIG. 3 and FIG. 7. For height and diameter values of nanostructure 102a in region 223, however, the angle of incidence of spectrum 201 may result in a small change in peak wavelength shift of reflected spectrum 202, relative to region 221. That is, region 223, including border line 222, may result in an angle independent or less angle dependent peak wavelength shift of reflected spectrum 202.

Figure 6A:
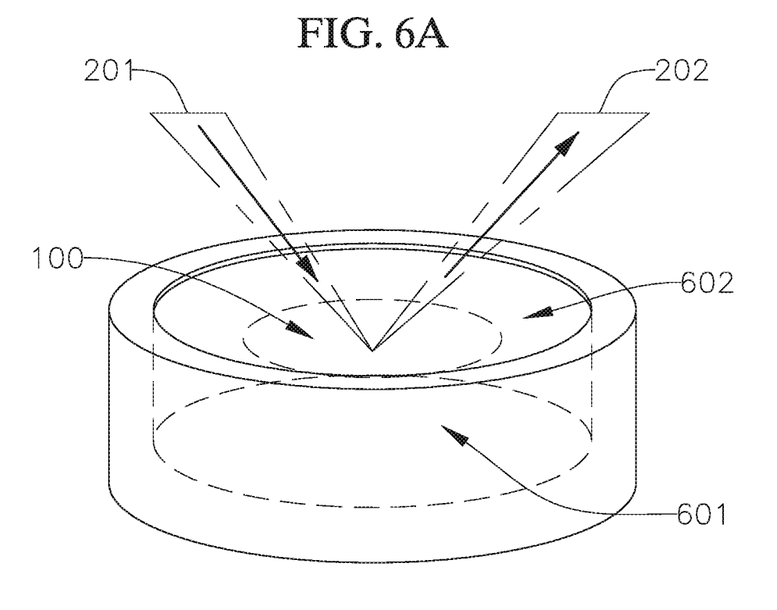
FIG. 6A depicts an example embodiment of a sensor with a top view.
Figure 6B:
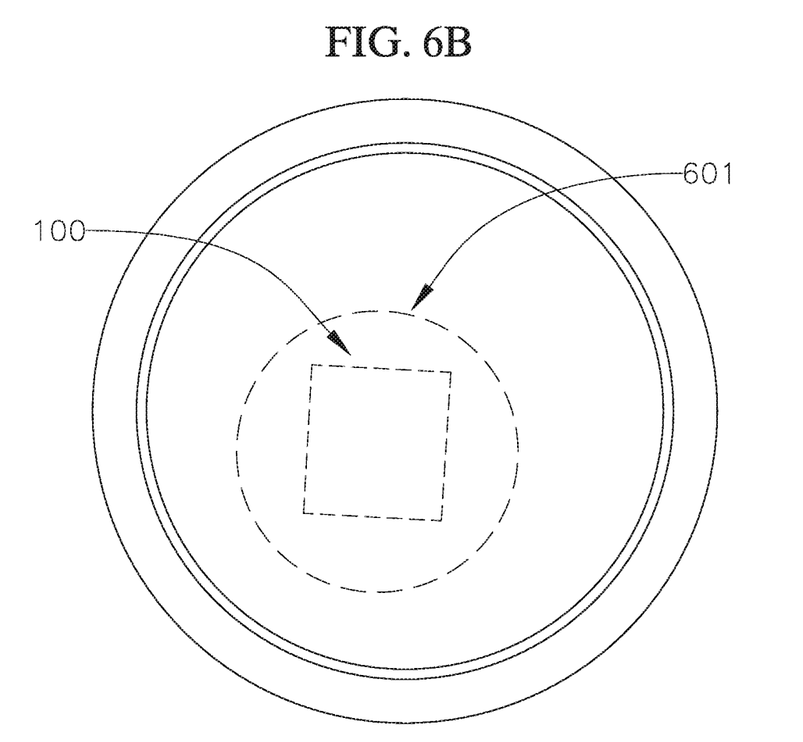
FIG. 6B depicts an example embodiment of a sensor with a side view.
Figure 7:
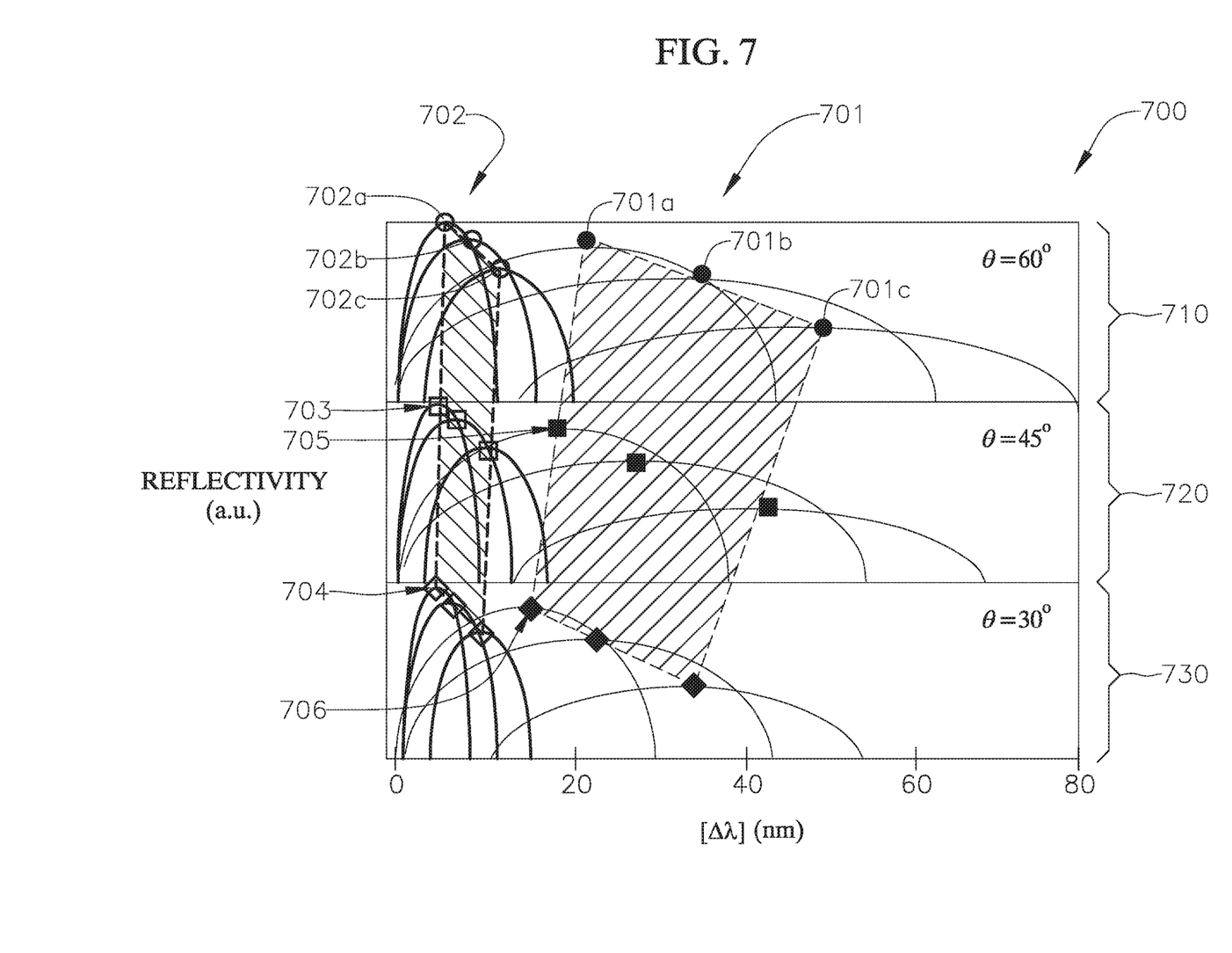
FIG. 7 depicts a pressure measurement by using change in peak wavelength of reflected spectrum of FIG. 2 of a structure of FIG. 6 with a first nanostructure type and second nanostructure type of FIG. 3 at varying pressures.

Furthermore, when performing measurements of peak wavelength shift of spectrum 202 for a normal-to-plane (i.e., angle independent) mode structure 100 of FIG. 1, it may be desirable to have a larger peak wavelength shift to more clearly read results from a sensor 600, which may be described in FIG. 6 and FIG. 7. The further away from the border line 222 into the normal-to-plane mode region, the less of a change in shift in peak wavelength that may occur. The less of a change in shift in peak wavelength that may occur, the more difficult it may be to perform measurements. The angle independent nature of structure 100 may not change, however, the ability to read measurements may be more difficult when the change in peak wavelength is smaller.

The physical parameters of height, diameter, and lattice constant of nanostructure 102a may impact the peak wavelength shift of the reflected spectrum 202, however, as long as the parameters enable a normal-to-plane mode, there may be little to no differences in the measured peak wavelength shift due to angle the angle of incidence (unlike values found in region 221). Therefore, it may be advantageous to select a height and diameter value that may be on border line 222.

The lattice constant, first distance 104, may be determined based on a target wavelength, which may be the peak wavelength reflected for reflected spectrum 202 and may be approximately ½ the target wavelength. For example, if a target wavelength is 620 nm, the lattice constant may be about 300 nm. For a range of diameter, height, and lattice constant values, a normal-to-plane mode may exist that may allow for reflected spectrum 202 to have a peak wavelength shift. In some ranges off and r, the peak wavelength shift for reflected spectrum 202 may be greater than for other ranges off and r.

In some embodiments, nanostructure 102a may comprise gold, f may be in the range of 0.4 to 0.8, and r may be in the range of 0.3 to 0.7. Therefore, 0.3*0.4 may be 0.12 and 0.8*0.7 may be 0.56, providing the ratio to be 12% to 56% of height of nanostructure 102a to first distance 104. In other embodiments, other ratios may exist. This embodiment may be for the visible spectrum for spectrum 201. In another embodiment, spectrum 201 may be near infrared (NIR), and other metals may be used, which may include gold, silver, or aluminum.

In another embodiment, nanostructure 102a may have a cross section in the Z-X plane that may be based on a paraboloid in shape, however, other shapes may be used, including square, rectangular, spherical, trapezoidal, hemi-ellipsoid, or other shape. A paraboloid may be a quadric surface with one axis of symmetry (Z axis for FIG. 2B), however, nanostructure 102a may not be exactly paraboloid in shape. It may have natural variations due to physical constraints of fabrication techniques, or it may be purposefully not fully paraboloid by design.

Nanostructure 102a may have a surface 205. Surface 205 may have a charge distribution 206. Surface 205 may have a surface plasmon (SP) mode, where the charge distribution 206 on the surface may oscillate between a positive and negative charge periodically, which may be known as periodicity. This may be known as a normal-to-plane mode which may be a resonant oscillation of conduction electrons that may occur along surface 205 of nanostructure 102a and may be according to a refractive index (RI) perceived by a wave at surface 205. The gradual increase of the RI along the Z axis may enable the normal-to-plane mode.

Without being bound by theory, it is believed that there may be an electric field polarized along the z-axis, as shown in FIG. 2B, which may be denoted as Ez. Similarly, there may be an electric field polarized along the x-axis, which may be denoted as Ex. There may be a dipole moment obtained from the Ez or the Ex electric field profiles. Ez may be oriented perpendicular and Ex may be oriented parallel to the plane of periodicity of pattern 103 on structure 100. That is, Ez may be along the z-axis and Ex may be along the x-axis. The dipole moment may be substantially less dependent on the first angle of incidence 203a of spectrum 201 and may be due to the surface plasmon mode.

A normal-to-plane mode may be along the z-axis, which may be a SP mode where the dipole moment of nanostructure 102a may be oriented normal to the plane of periodicity irrespective of the angle and polarization of spectrum 201. As described previously, this may result in angle-independence and polarization-independence, however, there may be some variations in response based on angle and polarization. The variations may be much less than for other (Non-paraboloid) nanostructure 102a shapes and patterns 103, which will be described further in FIG. 3.

Nanostructure 102a may have an effective plasmonic refractive index (RI) that varies based on the depth (z-axis) between the top and the bottom of nanostructure 102a. From the top of a nanostructure 102a and moving to the bottom of nanostructure 102a along the z-axis, there may be a gradual increase in the effective plasmonic RI. The effective plasmonic RI may be affected by neighboring nanostructures 102a-f of FIG. 1. As the first distance 104 increases between two nanostructures, the refractive index may decrease. As the first distance 104 decreases between two nanostructures, the refractive index may increase. Similarly, for two nanostructures, the base of the nanostructures are closer together than the tops of the nanostructures, along the z-axis. These differences in distance between the bottom and the top of two nanostructures may create an effective plasmonic RI gradient 207. An effective plasmonic RI gradient 207 may show a relationship between the depth from the top of nanostructure 102a to the base of nanostructure 102a. The effective plasmonic RI, $n_{eff}$, may be lower at the top of nanostructure 102a and may increase linearly along the surface 205 of nanostructure 102a.

Figure 3:
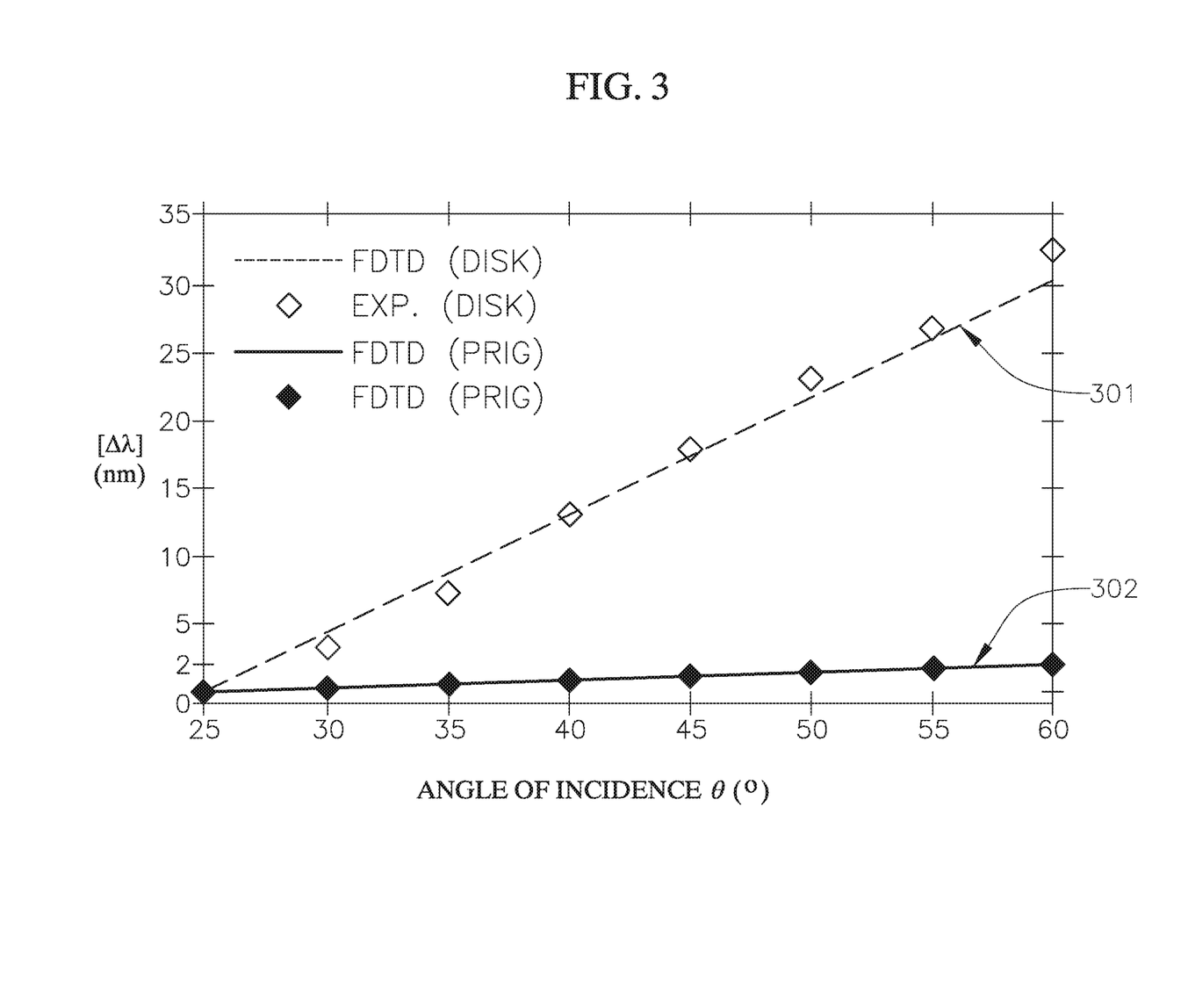
FIG. 3 depicts an example comparison of two differently-shaped nanostructures of FIG. 1.

FIG. 3 depicts an example comparison of two differently-shaped nanostructures 101 of FIG. 1. There may be an array of paraboloid-shaped nanostructures 101 and an array of disk-shaped nanostructures 101, which will be described in more detail below. The shape of nanostructures 101 may impact the change in wavelength dependence over a range of angles of incidence for input angles 203a to 203c. A paraboloid array may comprise paraboloid-shaped nanostructures 101 of FIG. 1 and may exhibit a normal-to-plane mode. A disk array may comprise disk-shaped nanostructures 101 of FIG. 1 and may exhibit an out-of-plane mode.

Spectrum 201 of FIG. 2 may have an input angle range 203a-c, which in the presently illustrated example may be shown as between 25 degrees to 60 degrees on the X-axis. Spectrum 201 may interact with nanostructures 101 on structure 100, and may result in a reflected spectrum 202 with a peak wavelength for each output angle 204a-c. The difference between the peak wavelength of reflected spectrum 202 at 25 degrees and angles higher than 25 degrees may be measured and denoted as Δλ on the Y-axis of FIG. 3, with units that may be in nanometers.

In some embodiments, for a first nanostructure type 301, which may be a non-paraboloid shape, has a difference between peak reflected spectrum 202 at 25 degree and angles higher than 25 degrees, and peak spectrum 201 may change linearly with input angle range 203a-c. For each five degree change in an input angle, there may be a 10% or greater change in Δλ. That is, there may be a change in Δλ that may be known as an angle-dependent response. For example, for a fixed spectrum 201, an input angle 203a may be 25 degrees and Δλ may be about 0 nm. An input angle 203b may be 40 degrees and Δλ may be about 14 nm. Input angle 203c may be 60 degrees and Δλ may be about 30 nm.

In another embodiment, second nanostructure type 302 may have a paraboloid shape and there may be a much more angle-independent response than for a disk shape structure in first nanostructure type 101. There may still be an angle-dependent response for second nanostructure type 302, however, relative to first nanostructure type 301, the response may be far less and the term angle-independence may be used. For example, for a fixed spectrum 201, an input angle 203a may be 25 degrees and Δλ may be about 0 nm. An input angle 203b may be 40 degrees and Δλ may also be about 1.4 nm Input angle 203c may be 60 degrees and Δλ may be 1.8 nm.

Figure 4:
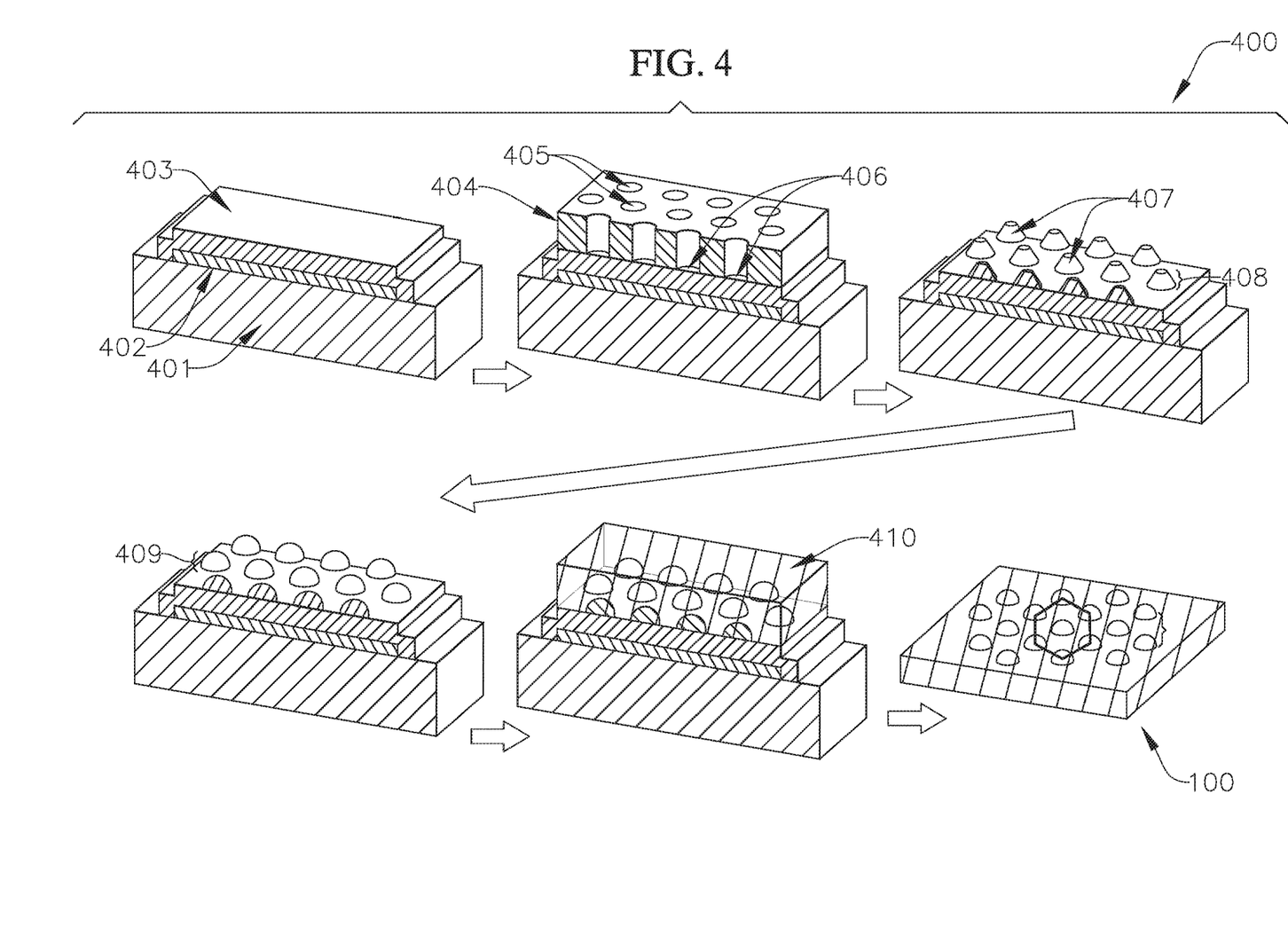
FIG. 4 depicts a fabrication process for fabrication of the nanostructure of FIG. 1.
Figure 5:
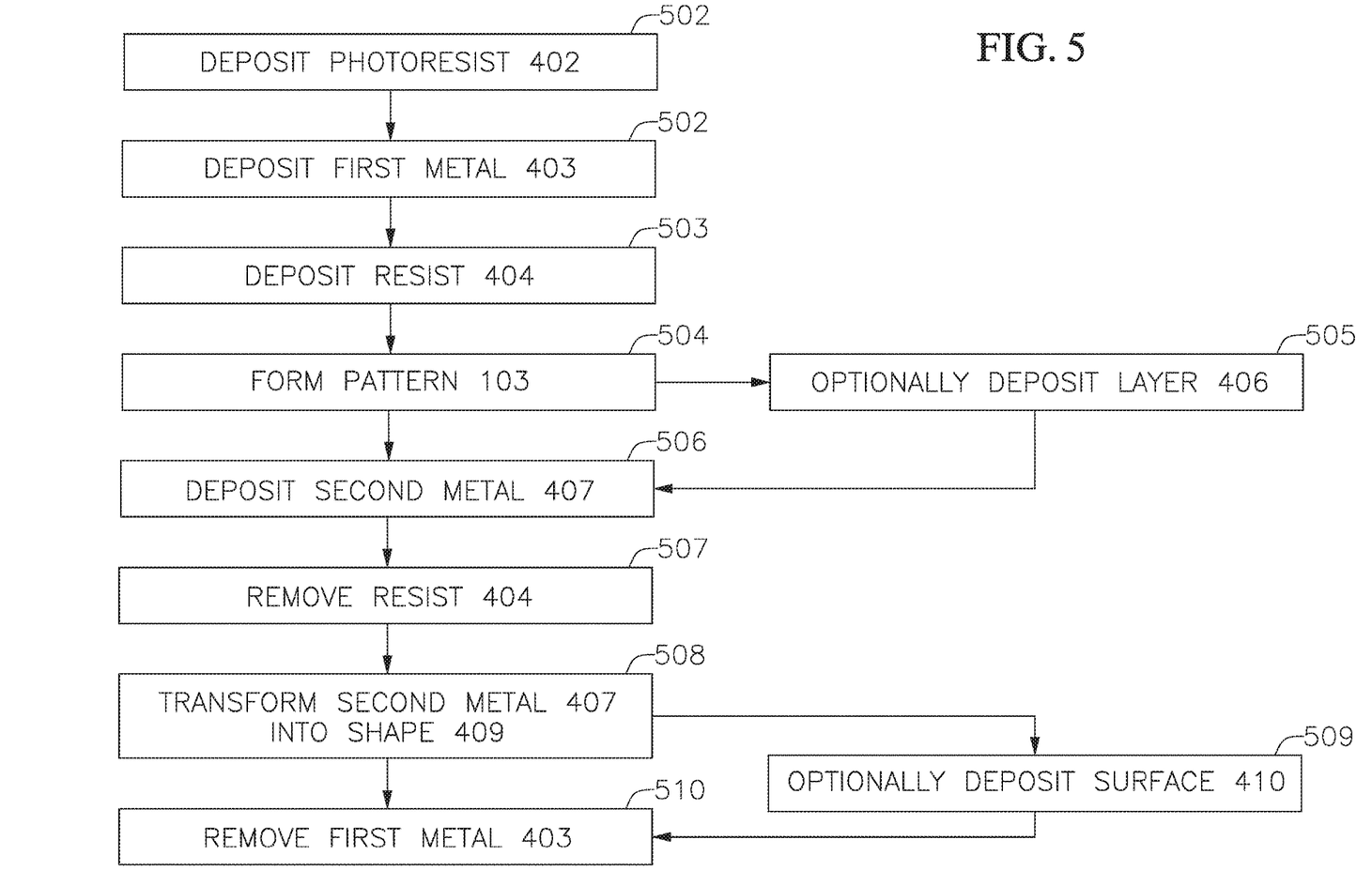
FIG. 5 depicts a process of fabrication process of FIG. 4.

FIG. 4 depicts a fabrication process 400 for fabrication of structure 100. FIG. 5 depicts a process 500 of fabrication process 400 of FIG. 4. Fabrication of structure 100 may begin on a substrate 401.

Substrate 401 may be any material upon which fabrication structure 100 may take place. In some embodiments, substrate 401 may be made from silicon. Substrate 401 may be a silicon wafer.

A photoresist 402 may be deposited onto substrate 401. This may be process 501 of FIG. 5: depositing photoresist 402 onto a substrate 401. In some embodiments, photoresist 402 may be about 1 micrometer (μm) thick. In another embodiment, photoresist 402 may be between 0.1μm and 5 μm thick. In some embodiments, photoresist 402 may be level and approximately equal in thickness across substrate 401.

Photoresist 402 may comprise a light-sensitive polymer material that may be used in a process to form a patterned coating on a surface, which patterning may also include removing all non-patterned photoresist 402 from a surface.

Photoresist 402 may have an associated sensitizer and solvent. In some embodiments, photoresist 402 may be used in a positive or a negative photoresist process. The chemical structures of photoresist 402 may be photopolymeric, photodecomposing, photocrosslinking, or any other photoresist structure. In another embodiment, the photoresist 402 may be exposed by electron beams.

In some embodiments, photoresist 402 may be spin coated onto substrate 401 to form a uniformly thick layer. In some embodiments, photoresist 402 may then be heated to between 100 C and 120 C for 100 seconds to 200 seconds.

Process 502 of FIG. 5 may comprise depositing a first metal 403 onto photoresist 402. First metal 403 may also be referred to as a substrate metal. In some embodiments, some of first metal 403 may also be deposited on substrate 401 in addition to photoresist 402. This may include a region between an edge of substrate 401 and an edge of photoresist 402. In another embodiment, all of first metal 403 may be deposited on photoresist 402.

In some embodiments, first metal layer 403 may be nickel. In another embodiment, first metal 403 may be any other metal in the periodic table, or a mixture or alloy of metals. In some embodiments, first metal layer 403 may be between 200 nm and 600 nm thick and may be used as a sacrificial layer. In some embodiments, first metal layer 403 may be deposited using electron beam (e-beam) evaporation. In some embodiments, the speed of evaporation of first metal 403 may be 0.05 nm/s to 5 nm/s.

Process 503 of FIG. 5 may comprise depositing resist 404 onto first metal layer 403. In some embodiments, resist 404 may be a synthetic resin, such as polymethyl methacrylate (PMMA). In another embodiment, resist 404 may be a ZEON electron beam positive-tone (ZEP) resist, as marketed and sold by ZEON SPECIALTY MATERIALS, INC. In another embodiment, resist 404 may be any kind of electron-beam resist.

In some embodiments, resist 404 may be spin coated onto first metal 403. In some embodiments, the time to bake resist 404 may be between 100 seconds and 200 seconds. In some embodiments, resist 404 may be baked at between 150 C and 200 C.

In some embodiments, resist 404 may be between 0.1 μm and 5 μm in thickness, however, the thickness of resist 404 may be larger or smaller and may depend on the target aspect ratio of holes 405. The thickness of resist 404 may depend on fabrication requirements, such as an aspect ratio of patterns formed on resist 404.

In some embodiments, electron beam (e-beam) lithography may be applied to resist 404 to form a pattern of holes, for forming the pattern 103 of FIG. 1. Process 504 of FIG. 5 may comprise forming pattern 103 on resist 404. The beam of the e-beam lithography may be between a 5 to 100 nano-amp beam with a power intensity of 1000-5000 microcoloumbs per cubic centimeter, and may be other values beyond this range.

The e-beam lithography applied to resist 404 may form holes 405 with a pattern 103. Holes 405 may expose first metal 403 at the location of holes 405. Pattern 103 of holes 405 may be used to aid in the formation of nanostructures 101. A hole of the holes 405 may have an aspect ratio, which may be the ratio of the height of the hole to the diameter of the hole. In some embodiments, the aspect ratio may be between 3 and 16.

In some embodiments, the diameter of a hole of the holes 405 may be between 100 nm and 1 μm, however, the diameter of the hole may be greater or smaller depending on the target wavelength application. In some embodiments, the diameter of a hole in holes 405 may be within an order of magnitude of the target wavelength application. In another embodiment, there may be multiple diameters of holes used in holes 405.

In some embodiments, a layer 406 may be deposited onto first metal 403 at the location of holes 405. Process 505 of FIG. 5 may comprise optionally depositing layer 406 onto first metal 403. Layer 406 may be an adhesion layer and may be used to aid in the deposition process of metals. Layer 406 may be a metal, such as chromium, and may be between 1 nm and 5 nm in thickness. Layer 406 may also be known as an adhesion layer. Layer 406 may allow for better adhesion between first metal 403 and a second metal 407.

A second metal 407 may be deposited onto part of or all of layer 406 at the location of holes 405, which may be the same location as pattern 103 and may form pattern 103. Second metal 407 may also be referred to as a nanostructure metal. In another embodiment, where first metal 403 is not used, second metal 407 may be deposited onto any substrate at the location of holes 405. Process 506 of FIG. 5 comprises depositing second metal 407 at the location of holes 405. In another embodiment, second metal 407 may be deposited onto first metal 403 at the location of holes 405 when layer 406 is not present. In some embodiments, second metal 407 may be gold, however, it may be other metals, including aluminum, silver, copper, aluminum-doped zinc oxide, indium tin oxide, titanium nitride, indium gallium arsenide, tungsten oxide, titanium-tungsten or any other metals or metal alloys. In some embodiments, second metal 407 is between 50 nm and 500 nm thick, but may be other thicknesses depending on the target wavelength application, as described previously. A target wavelength application may be the wavelength at which nanostructures 101 interact with the target wavelength and may be the peak wavelength reflected in reflected spectrum 202 of FIG. 2A. In some embodiments, the second metal 407 chosen may depend on the target wavelength. For visible spectrum, second metal 407 may be gold, but it may be other metals. For NIR spectrum, second metal 407 may be aluminum or silver, but it may be other metals. The spectrum range a metal reflects at may be used to determine the metal to select for the target wavelength. Gold may be able to reflect visible spectrum, whereas aluminum and silver may be able to reflect NIR spectrum.

In some embodiments, second metal 407 may be deposited using e-beam deposition, however, other deposition methods may be used.

Second metal 407, once deposited, may be initially in a shape 408. In some embodiments, shape 408 may be a cone shape. The top of the cone may be flat or level, and may not finish at a singular point. The cone shape may be formed as a result of the aspect ratio of holes 405. If the aspect ratio is low, shape 408 may look more like a disk. If the aspect ratio is high, shape 408 may look more like a cone with a sharp, singular point as its tip. As will be described below, the shaping of first metal 407 from shape 408 into a shape 409 may occur after resist 404 is removed.

In some embodiments, resist 404 may be removed. Process 507 of FIG. 5 comprises removing resist 404. Resist 404 may be removed with a lift-off bath method using a solvent stripper such as REMOVER PG, as marketed and sold by KAYUKA ADVANCED MATERIALS. REMOVER PG may be used and resist 404 may be in a lift-off bath for 6 to 30 hours. In another embodiment, a different method may be used to remove resist 404.

Second metal 407 may be in shape 408 and without resist 404 may be transformed to shape 409. Process 508 of FIG. 5 may comprise transforming second metal 407 from shape 408 to shape 409. In some embodiments, shape 409 may be paraboloid in shape. In another embodiment, shape 409 may be a disk, cone, or hemi-sphere. In some embodiments, exposure to an ion beam may be used to shape second metal 407 from shape 408 to shape 409.

Focused-ion beam exposure may be used to form second metal 407 into shape 409, with a 0.1 to 2 nano-Amp beam which may have a 0.01 to 1 millisecond dwell time. Dwell time may be the exposure time of the ion beam to second metal 407. The focused-ion beam may be a directional beam, which may allow for the edges of the second metal 407 shape 408 to wear off. That is, the focused-ion beam may be directional, which may be perpendicular to the substrate 401 in some embodiments. The sharp features facing the focused-ion beam directions, such as edges, points, or flat surfaces, may be removed. In some embodiments, the direction of the ion beam may be at an angle between 0 degrees (parallel) and 90 degrees (perpendicular) to substrate 401. In some embodiments, the direction may not change during the dwell time where the ion beam is being exposed. In another embodiment, the direction may change during the dwell time where the ion beam is being exposed.

Process 509 of FIG. 5 may comprise optionally depositing surface 410 onto second metal 407. In some embodiments, surface 410 may be PDMS and may be deposited via spin coating, however, it may be other materials, such as those that are elastic or that may allow waves to travel through it and may be deposited by another technique. In some embodiments, surface 410 may be between 1 and 100 times the height of second metal 407. Surface 410 may be an optional surface and may not be deposited onto second metal 407 in some embodiments.

In some embodiments, first metal 403 may extend beyond the base of photoresist 402. This extended area may be cut away and the structure of photoresist 402, first metal 403, layer 406 (if included in the deposition process), second metal 407, and surface 410 may be removed from substrate 401. Photoresist 402 may then be removed by using a solvent, such as acetone. In some embodiments, acetone solvent may be used for between 2 and 10 minutes to remove photoresist 402.

In some embodiments, when structure 100 comprises nanostructures 101 of FIG. 1 embedded in surface 410, first metal 403 may be removed with an acid bath. Process 510 of FIG. 5 may comprise removing first metal 403. In some embodiments, there may be a cut on the sides of first metal 403 that exposes photoresist 402 and layer 404 (when present), and an acid bath may be used to remove layers from the bottom up. That is, photoresist layer 402 may be removed, followed by layer 403, and followed by layer 404 when present. Hydrochloric acid may be used and the structure may be in an acid bath for between 12 and 36 hours. In another embodiment, first metal 403 may be removed with alternate methods. The resulting structure may be structure 100 which may comprise layer 406, second metal 407, and surface 410. In another embodiment, layer 406 may also be removed using the hydrochloric acid bath.

In another embodiment, first metal 403 and layer 402 may not be needed and the resulting structure may be directly fabricated on 401. Subsequently, process 502 and process 503 may not occur. This embodiment may be for a structure 100 where nanostructures 101 are exposed and are on the surface of substrate 401 with no surface 410 present. In this embodiment, process 510 may not occur and no acid bath may be used. Instead, substrate 401 may be cut to form structure 100.

The resulting structure may be structure 100 which may comprise second metal 407, and surface 410.

In another embodiment, structure 100 may comprise second metal 407 and surface 410 when layer 406 is not used.

FIG. 6 depicts an example embodiment of a sensor 600 with a top view and side view. Sensor 600 may use structure 100 to measure a change in pressure. Sensor 600 may comprise a cavity 601. A membrane 602 may be on the top side of cavity 601. Structure 100 may be on membrane 602.

Cavity 601 may be an elastomeric material, such as PDMS. Cavity 601 may be filled with a compressible fluid at a known pressure, such as air, and sealed so that if immersed in a fluid, no fluid may penetrate cavity 601. In some embodiments, cavity 601 may be a cylinder with a height of between 10 μm to 1 mm and diameter of between 100 μm and 5 mm. Structure 100 may be attached to cavity 601 on the surface of membrane 602, or it may be embedded in membrane 602.

In some embodiments, membrane 602 may deflect based on a pressure differential of the outside relative to the inside. A spectrum 201 may be transmitted to structure 100, which may be reflected as a reflected spectrum 202, which may have an associated peak wavelength that is reflected. The peak wavelength reflected in reflected spectrum 202 at an unknown pressure may be compared to the peak wavelength observed when the pressure differential is known to determine a pressure change in membrane 602.

Specifically, cavity 601 may experience a pressure differential between its internal cavity 601 fluid and the external environment, which may deflect membrane 602. The deflection of membrane 602 may result in radial strain on structure 100, which may cause the nanostructures 101 embedded within structure 100 to become more or less tightly spaced. This in turn causes a change in peak wavelength, which may be used to estimate the pressure differential, as will be described in FIG. 7. In some embodiments, cavity 601 may be placed in the anterior chamber of an eye, in a position that may be outside of the field of view. An eye pressure change may lead to a pressure change in cavity 601, which may in turn cause membrane 602 to deflect and structure 100 to deflect.

While the previously described embodiment focuses on a pressure sensor using structure 100 and cavity 601, structure 100 may also be used without cavity 601. In another embodiment, membrane 602 and structure 100 may form a sensor without cavity 601. Structure 100 may be embedded in membrane 602, or may be placed on top of membrane 602. With structure 100 embedded in membrane 602, the resulting configuration may be used as a sensor for measuring the stretch or compression of the material when placed on a surface. With structure 100 placed on top of membrane 602, the resulting structure may be used to detect the composition of a material or liquid placed on top of or in direct contact with structure 100.

FIG. 7 depicts a pressure measurement 700 of sensor 600 of FIG. 6 with structure 100. FIG. 7 may compare the change in peak wavelength of reflected spectrum 202 at varying pressures for structures 100 with a first nanostructure type 301 and a second nanostructure type 302 of FIG. 3. FIG. 7 may illustrate an advantage of using paraboloid shaped nanostructures. The x-axis may show a change in wavelength |Δλ| in nm. The y-axis may show a reflectivity of reflected spectrum 202 in arbitrary units (a.u.). Reflection may be measured in photon counts that may be measured by a spectrometer. The photon count may vary depending on the physical environment, light source power, and other variables. Therefore, a.u. may be used for analyzing the reflectivity and to compare a peak wavelength shift.

A change in peak wavelength of reflected spectrum 202 for a first nanostructure type 301 at varying pressure levels and varying angles of incidence 203*a-c* of FIG. 2A may be depicted in responses 701. A change in peak wavelength of reflected spectrum 202 for a second nanostructure type 302 at varying pressure levels and varying angles of incidence 203a-c of FIG. 2A may be depicted in responses 702. As described in FIG. 3, first nanostructure type 301 may comprise disk or other non-paraboloid shapes. Second nanostructure type 302 may comprise paraboloid-shaped nanostructures.

FIG. 7 may show three angles of incidences for spectrum 201 of FIG. 2 in scenarios 710, 720, and 730. In scenario 710, the angle of incidence may be 60 degrees. In scenario 720, the angle of incidence may be 45 degrees, and in scenario 730, the angle of incidence may be 30degrees. Scenarios 710, 720, and 730 may correspond to input angles 203a-c of FIG. 2 (e.g., 710 to 203c, 720 to 203b, 730 to 203a).

For each scenario 710, 720, and 730, and for both responses 702 and 701, there may be three sets of peak wavelength changes that may correspond to pressures in sensor 600 of 0 mmHg (i.e., no pressure change), 20 mmHg, and 40 mmHg. For each set of three graph lines, the topmost graph line may correspond to 0 mmHg pressure change, the middle graph line may represent a 20mmHg pressure change, and the lowest graph line may represent 40 mmHg pressure change. For example, measurement 702a may show a peak wavelength shift for second nanostructure type 302 when sensor 600 is calibrated to 0 mmHg pressure change.

Referring to scenario 710, there are responses 702 and 701 for an angle of incidence of 60degrees. In response 702, which may correspond to second nanostructure type 302, within scenario 710, there may be three profiles of corresponding peak wavelength shifts, shown as measurements 702a-c. Measurement 702a may correspond to a pressure change of 0 mmHg. Measurement 702b may correspond to a pressure change of 20 mmHg, and measurement 702c may correspond to a pressure change of 40 mmHg.

Similarly, for response 701, referring to scenario 710, measurement 701a may have a pressure change of 0 mmHg, measurement 701b may have a pressure change of 20 mmHg, and measurement 701c may have a pressure change of 40 mmHg.

Referring to the 0 mmHg pressure change of response 702 across multiple angles of incidences, corresponding to scenarios 710, 720, and 730, there may be peak wavelength shift 702a in scenario 710, peak wavelength shift 703 in scenario 720, and peak wavelength shift 704 in scenario 730. Peak wavelength shift 702a may be approximately 3 nm, peak wavelength shift 703 may be approximately 2.75 nm, and peak wavelength shift 704 may be approximately 2.5 nm.

Referring to the 0 mmHg pressure change of response 701, there may be a peak wavelength shift 701a in scenario 710, 705 in scenario 720, and 706 in scenario 730. Peak wavelength shift 701a may be approximately 25 nm, peak wavelength shift 705 may be approximately 18 nm, and peak wavelength shift 706 may be approximately 15 nm. Reviewing the other pressure change responses 701 and 702, one may find that response 702 may have an angle-independent response (e.g., very little peak wavelength shift) to a change in peak wavelength of spectrum 202. As described previously, angle independent may be less angle-dependent than other solutions. Response 702, which may use paraboloid-shaped nanostructures of second nanostructure shape 302, may have a peak wavelength shift at 0 mmHg of between 2.5 nm and 3 mm for angle of incidence ranges from 30 degrees of scenario 730 to 60 degrees of scenario 710, respectively. The difference in peak wavelength shift between a 30 degree and 60 degree angle of incidence may be approximately 0.5 nm. In the visible spectrum, a difference in peak wavelength shift of 0.5 nm may not result in a color change. Therefore, if a paraboloid-shaped nanostructure is used in sensor 600, there may be an "angle independent" range where measurements may provide approximately the same readings across a range of angles of incidence.

Meanwhile, response 701, which may use first nanostructure type 301, which use disc-shaped nanostructures, may show an angle-dependent response to peak wavelength shifts 701a, 704, and 706. Response 701 may have a peak wavelength shift at 0 mmHg of between 15 nm and 25 nm for angle of incidence ranges from 30 degrees of scenario 730 to 60 degrees of scenario 710. The difference in peak wavelength shift between a 30 degree and 60 degree angle of incidence may be approximately 10 nm. In the visible spectrum, a difference in peak wavelength shift of 10 nm may result in a color change. Therefore, if a disc-shaped nanostructure is used in sensor 600, there may be an "angle dependent" range where measurements may provide different readings across a range of angles of incidence.

As described previously, paraboloid-shaped nanostructures may allow for a useful sensor 600 because it may be angle independent or less dependent on angles of incidence. The angle of incidence of spectrum 201 may not need to be exact and it may be a range of angles, such as from 30 degrees to 60 degrees. This may be shown in responses 702. Unlike responses 701, in responses 701, there may be an angle dependent response which may not be useful for a sensor 600 because measurements may require an exact angle of incidence to provide repeatable measurements.

Pressure measurement readings may be calibrated for sensor 600 by using the data of pressure measurement 700, specifically responses 702.

Sensor 600 may use paraboloid-shaped nanostructures and may be calibrated to pressure measurements as shown in responses 702. That is, for a given pressure change, there may be one peak wavelength shift regardless of the angle of incidence of spectrum 201. As shown in the shaded region of responses 702, the peak wavelength shift for each pressure change is different across pressure and about the same across angles of incidence. Therefore, a problem that was previously intractable, measuring pressure across a range of angles of incidence, may now be solvable and used in sensor 600.

Example embodiments of the invention concept may extend to the following statements, without limitation:

Statement 1: a metamaterial structure, comprising: a substrate, and nanostructures located in a pattern on or within the substrate, wherein the nanostructures are paraboloid in shape and arranged in a periodic pattern.

Statement 2: the structure of statement 1, wherein the nanostructures are capable of operating in normal-to-plane mode, wherein the normal-to-plane mode further comprises an angle-independent surface plasmon mode and polarization-independent surface plasmon mode.

Statement 3: the structure of statement 1, wherein the nanostructures are comprised one or more of the following: gold, aluminum, silver, copper, aluminum-doped zinc oxide, indium tin oxide, titanium nitride, indium gallium arsenide, tungsten oxide, or titanium-tungsten, or a combination thereof.

Statement 4: the structure of statement 1, wherein the metamaterial substrate is flexible or stretchable.

Statement 5: the structure of statement 1, wherein the nanostructures shape is hemi-ellipsoid or paraboloid shaped.

Statement 6: the structure of statement 1, wherein the nanostructures are arranged in a semi-periodic pattern comprising both equidistant nanostructures and non-equidistant nanostructures.

Statement 7: the structure of statement 1, wherein the distance between closest nanostructures is between 60 nm and 600 nm.

Statement 8: the structure of statement 1, wherein the distance between closest nanostructures is between 120 nm and 1200 nm.

Statement 9: the structure of statement 1, wherein the diameter of the nanostructures is between 10 nm and 2000 nm.

Statement 10: the structure of statement 1, wherein the height of the nanostructures is between 36 nm and 168 nm.

Statement 11: the structure of statement 1, wherein the periodic pattern is hexagonal.

Statement 12: the structure of statement 1, wherein the periodic pattern is square.

Statement 13: a method to fabricate a metamaterial surface, comprising: depositing a nanostructure metal on a substrate, and forming paraboloids from the nanostructure metal.

Statement 14: the method of statement 13, further comprising: depositing a resist before depositing the nanostructure metal, forming a pattern of holes in the resist before depositing the nanostructure metal.

Statement 15: the method of statement 13, further comprising: depositing a flexible material surface on to the nanostructure metal.

Statement 16: the method of statement 13, further comprising: depositing a substrate metal before depositing the nanostructure metal, and dissolving the substrate metal after forming the paraboloids from the nanostructure metal.

Statement 17: the method of statement 16, wherein the substrate metal is between 200 nm and 600 nm thick.

Statement 18: the method of statement 13, further comprising: depositing a photoresist before the nanostructure metal is deposited, and removing the photoresist after the nanostructure metal is deposited.

Statement 19: the method of statement 14, further comprising depositing an adhesion layer before the nanostructure metal is deposited.

Statement 20: the method of statement 19, wherein the adhesion layer is chromium.

Statement 21: the method of statement 14, wherein the holes have an aspect ratio of between 3 and 16.

Statement 22: the method of statement 13, wherein the nanostructure metal is between 50 nm and 500 nm thick.

Statement 23: the method of statement 13, wherein the nanostructure metal comprises one or more of: gold, aluminum, silver, copper, aluminum-doped zinc oxide, indium tin oxide, titanium nitride, indium gallium arsenide, tungsten oxide, or titanium-tungsten, or a combination thereof.

Statement 24: a method to determine pressure changes, comprising: receiving a wavelength spectrum on a metamaterial structure, measuring a peak wavelength reflected from the metamaterial, and comparing the peak wavelength reflected to a reference point.

Statement 25: a pressure sensor, comprising: a metamaterial, a cavity, wherein the metamaterial further comprises nanostructures located in a pattern, are paraboloid shaped, and are periodic.

The invention claimed is:

1. A metamaterial structure, comprising:
a substrate, and
nanostructures located in a pattern on or within the substrate, wherein:
the nanostructures are paraboloid shaped, arranged in a periodic pattern, and reflect a target wavelength of a spectrum of light at a greater intensity than other wavelengths of the spectrum of light;
a range of height values and a range of diameter values are identified based on a determination of height values and diameter values that result in a change in peak wavelength shift of less than five nanometers over a range of angles of incidence of the spectrum of light; and
at least one of a height or a diameter of a paraboloid element of the nanostructures is selected from the range of height values and the range of diameter values.

2. The metamaterial structure of claim 1, wherein the nanostructures are capable of operating in normal-to-plane mode, wherein the normal-to-plane mode further comprises an angle-independent surface plasmon mode and a polarization-independent surface plasmon mode.

3. The metamaterial structure of claim 2, wherein a dipole moment of the nanostructures is oriented normal to a plane of periodicity of the nanostructures based on the nanostructures operating in the normal-to-plane mode.

4. The metamaterial structure of claim 1, wherein the nanostructures comprise gold, aluminum, silver, copper, aluminum-doped zinc oxide, indium tin oxide, titanium nitride, indium gallium arsenide, tungsten oxide, titanium-tungsten, or a combination thereof.

5. The metamaterial structure of claim 1, wherein the substrate is flexible or stretchable.

6. The metamaterial structure of claim 1, wherein a distance between closest nanostructures is between 60 nm and 600 nm.

7. The metamaterial structure of claim 1, wherein a distance between closest nanostructures is between 120 nm and 1200 nm.

8. The metamaterial structure of claim 1, wherein a diameter of the nanostructures is between 10 nm and 2000 nm.

9. The metamaterial structure of claim 1, wherein a height of the nanostructures is between 36 nm and 168 nm.

10. The metamaterial structure of claim 1, wherein the periodic pattern is hexagonal.

11. The metamaterial structure of claim 1, wherein the periodic pattern is square.

12. The metamaterial structure of claim 1, wherein the periodic pattern comprises a triangular shape.

13. The metamaterial structure of claim 12, wherein the periodic pattern comprises an equilateral triangular shape.

14. The metamaterial structure of claim 12, wherein the periodic pattern comprises an isosceles triangular shape.

15. The metamaterial structure of claim 1, wherein:
the range of height values and the range of diameter values are determined based on comparing varying instances of a filling factor to varying instances of an aspect ratio;
the varying instances of the filling factor comprise at least a first filling factor of a first diameter value relative to a fixed lattice constant value and a second filling factor of a second diameter relative to the fixed lattice constant value; and
the varying instances of the aspect ratio comprise at least a first aspect ratio of a first height value relative to the first diameter value and a second aspect ratio of a second height value relative to the second diameter value.

16. The metamaterial structure of claim 1, wherein the range of angles of incidence vary from 25 degrees to 60 degrees.

\* \* \* \* \*